US012708216B1

(12) United States Patent
Van Erlach

(10) Patent No.: US 12,708,216 B1
(45) Date of Patent: Aug. 18, 2026

(54) ENHANCED MOTION-ENABLED SLEEP SURFACE

(71) Applicant: Nexxus Wealth Technologies, Inc., Walnut, CA (US)

(72) Inventor: Julian Van Erlach, Walnut, CA (US)

(73) Assignee: NEXXUS WEALTH TECHNOLOGIES, INC., Walnut, CA (US)

( * ) Notice: Subject to any disclaimer, the term of this patent is extended or adjusted under 35 U.S.C. 154(b) by 0 days.

(21) Appl. No.: 19/382,775

(22) Filed: Nov. 7, 2025

Related U.S. Application Data

(60) Provisional application No. 63/776,754, filed on Mar. 24, 2025.

(51) Int. Cl.
*A47C 20/04* (2006.01)
*A47C 21/00* (2006.01)
(Continued)

(52) U.S. Cl.
CPC ............ *A47C 20/04* (2013.01); *A47C 21/006* (2013.01); *A47C 31/123* (2013.01); *A47D 9/02* (2013.01); *A61B 5/165* (2013.01); *A61B 5/4812* (2013.01); *A61B 5/4818* (2013.01); *A61B 5/746* (2013.01); *A61H 1/003* (2013.01); *A61M 21/02* (2013.01); *A61M 2021/0022* (2013.01)

(58) Field of Classification Search
CPC ..... A47C 20/04; A47C 21/006; A47C 31/123; A47D 9/02; A61B 5/165; A61B 5/4812; A61B 5/4818; A61B 5/746; A61M 21/02; A61M 2021/0022; A61H 1/001; A61H 1/003
USPC ..... 5/105, 108, 109, 609, 610, 915; 601/100
See application file for complete search history.

(56) References Cited

U.S. PATENT DOCUMENTS 4,258,446 A * 3/1981 McAllister ............. A47D 9/057 5/105
4,277,857 A * 7/1981 Svehaug ............. A47C 21/006 5/108

(Continued)

FOREIGN PATENT DOCUMENTS

KR 101731220 B1 * 5/2017 ........... A47C 21/006

OTHER PUBLICATIONS

Machine Translation of KR-101731220-B1.*

(Continued)

*Primary Examiner* — David R Hare
(74) *Attorney, Agent, or Firm* — Schmeiser Olsen PLLC

(57) ABSTRACT

A method, system, and computer program product for moving an upper frame disposed within a rocking bed structure. The upper frame is moved in accordance with at least one motion namely a rocking motion, a vertical motion, or both the rocking and vertical motions. Each motion of the at least one motion includes each phase of the following phases (i), (ii), (iii) and (iv) occurring at least once: (i) a point on the upper frame accelerates from a first endpoint to a mid-cycle range of locations between the first endpoint and a second endpoint; (ii) the point on the upper frame decelerates from the mid-cycle range of locations to the second endpoint; (iii) the point on the upper frame accelerates from the second endpoint to the mid-cycle range of locations; and (iv) the point on the upper frame decelerates from the mid-cycle range locations to the first endpoint.

28 Claims, 7 Drawing Sheets

(51) Int. Cl.

| | |
|---|---|
| ***A47C 31/12*** | (2006.01) |
| ***A47D 9/02*** | (2006.01) |
| ***A61B 5/00*** | (2006.01) |
| ***A61B 5/16*** | (2006.01) |
| ***A61H 1/00*** | (2006.01) |
| ***A61M 21/00*** | (2006.01) |
| ***A61M 21/02*** | (2006.01) |

(56) References Cited

U.S. PATENT DOCUMENTS 5,228,155 A * 7/1993 Shultz .................... A47D 9/057 5/109
5,301,661 A * 4/1994 Lloyd .................... A61H 1/001 601/87
7,211,058 B1 * 5/2007 Chung .................... A61H 1/003 601/101
7,281,284 B2 * 10/2007 Sims, Jr. .............. A47C 21/006 5/607
7,478,446 B2 * 1/2009 Sims, Jr. .............. A47C 21/006 5/607
8,029,377 B2 * 10/2011 Velderman ........... A47D 13/107 5/108
8,561,227 B2 * 10/2013 Jenkins .................... A47D 9/04 5/108
8,707,477 B1 * 4/2014 Flemister ............. A47C 21/006 5/108
8,789,220 B2 7/2014 Flemister
9,888,784 B2 2/2018 Chapin
10,447,972 B2 10/2019 Patil
10,463,168 B2 11/2019 Karp et al.
11,123,515 B2 9/2021 Karp et al.
11,812,858 B1 * 11/2023 Plemmons ........... A47C 21/003
12,446,704 B2 * 10/2025 Wu ........................ A61H 1/005
2004/0215113 A1 * 10/2004 Saringer .............. A61G 7/0573 601/103
2009/0211022 A1 8/2009 Harding
2012/0216347 A1 * 8/2012 Tundo .................... A47D 9/057 74/25
2013/0007958 A1 * 1/2013 Flemister ............... A61G 7/005 5/609
2015/0045608 A1 * 2/2015 Karp ..................... A61M 21/02 5/655
2017/0318978 A1 11/2017 Flemister
2019/0223612 A1 7/2019 Wattereson et al.
2023/0255360 A1 8/2023 Srinivasan et al.
2023/0270261 A1 * 8/2023 Kamei ................. A47C 21/006 5/609
2023/0346125 A1 11/2023 Kato et al.

OTHER PUBLICATIONS

Smart AI-Enabled Device and System for Head-Toe Rocking of a Surface, May 5, 2024, 25 pages.

Van Sluijs et al., Gentle rocking movements during sleep in the elderly, DOI: 10.1111/jsr.12989, Revised: Jan. 13, 2020, Accepted: Jan. 16, 2020, Retrieved from: https://pmc.ncbi.nlm.nih.gov/articles/PMC7757236/, 8 pages.

Breuss, et al., Enhancing Sleep Quality with Closed-Loop Autotuning of a Robotic Bed, 2023 International Conference on Rehabilitation Robotics (ICORR), Singapore, Singapore, 2023, pp. 1-6, doi: 10.1109/ICORR58425.2023.10304729.

Perry et al., Sleep in Motion 'cruises' in adjustable bed arena, Retrieved from: https://www.furnituretoday.com/business-news/sleep-motion-cruises-adjustable-bed-arenal, Jan. 19, 2017, 4 pages.

* cited by examiner

ENHANCED MOTION-ENABLED SLEEP SURFACE

RELATED APPLICATIONS

The present invention claims priority to U.S. Provisional No. 63/776,754, filed on Mar. 24, 2025, which is incorporated herein by reference in its entirety.

TECHNICAL FIELD

Embodiments of the present invention relate generally to a rocking bed structure, and more specifically to surface motions within the rocking bed structure BACKGROUND Studies show that motion appears beneficial in inducing sleep and improving sleep quality as well as providing other health benefits.

SUMMARY

Embodiments of the present invention provide a system. The system comprises: a rocking bed structure that includes an upper frame and one or more actuators configured to move the upper frame in accordance with at least one motion selected from the group consisting of a rocking motion, a vertical motion, or both the rocking motion and the vertical motion, wherein each motion of the at least one motion includes each phase of the following phases (i), (ii), (iii) and (iv) occurring at least once: (i) a point on the upper frame accelerates from a first endpoint to a mid-cycle range of locations between the first endpoint and a second endpoint; (ii) the point on the upper frame decelerates from the mid-cycle range of locations to the second endpoint; (iii) the point on the upper frame accelerates from the second endpoint to the mid-cycle range of locations; and (iv) the point on the upper frame decelerates from the mid-cycle range locations to the first endpoint.

Embodiments of the present invention provide a method, and an associated computer program product, for moving an upper frame disposed within a rocking bed. The method comprises: moving the upper frame in accordance with at least one motion selected from the group consisting of a rocking motion, a vertical motion, and both the rocking motion and the vertical motion, wherein each motion of the at least one motion includes each phase of the following phases (i), (ii), (iii) and (iv) occurring at least once: (i) a point on the upper frame accelerates from a first endpoint to a mid-cycle range of locations between the first endpoint and a second endpoint; (ii) the point on the upper frame decelerates from the mid-cycle range of locations to the second endpoint; (iii) the point on the upper frame accelerates from the second endpoint to the mid-cycle range of locations; and (iv) the point on the upper frame decelerates from the mid-cycle range locations to the first endpoint.

DETAILED DESCRIPTION

Figure 1:
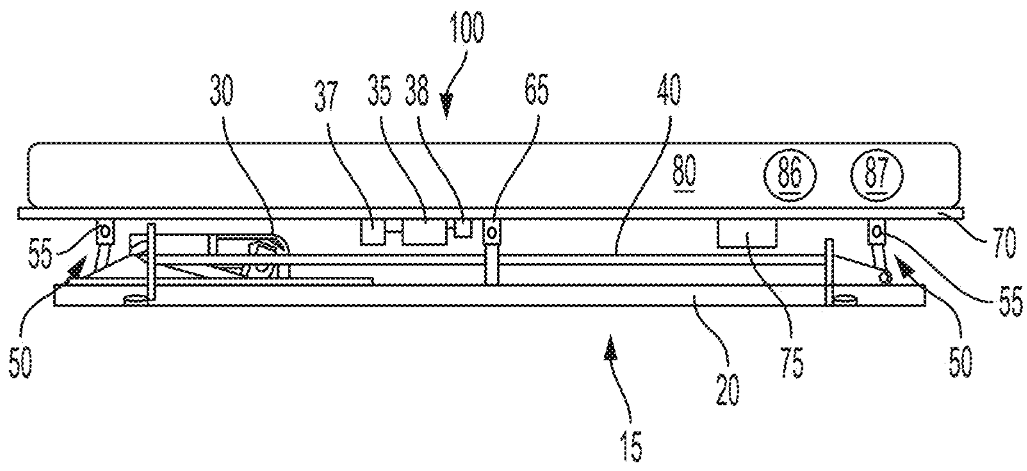
FIG. 1 depicts a side view of a rocking bed structure comprising a base frame structure, an upper frame, and a mattress, in accordance with embodiments of the present invention.

Embodiments of the present invention provide a powered movable surface capable of novel rocking motions and/or vertical motions individually or in combination, characterized by acceleration and deceleration profiles based on aspects of the respective rocking or vertical cycles of motion. The surface may be a surface of a device such as, inter alia, a bed, adjustable bed base, crib or seat. Cycles of motion of the rocking motions and/or vertical motions are characterized by endpoints. The word "endpoint", as used herein, means an endpoint of motion direction at which the direction of motion reverses and from which the opposite direction of motion commences. Each cycle of the cycles of motion has two endpoints, namely an apex (i.e., the highest point of the cycle) and a nadir (i.e., the lowest point of the cycle).

Each cycle also has a mid-cycle range of continuously distributed points that exists between the two endpoints, wherein the mid-cycle range may be: equidistant from the apex and the nadir, closer to the apex than to the nadir, or closer to the nadir than to the apex.

Acceleration profiles increase from the endpoints upon commencement of motion in the opposite direction from the acceleration which preceded the endpoint (e.g., the apex) and decrease from the midrange of each cycle until the opposite endpoint (e.g., the nadir) is reached whereupon a perceptible pause may occur to ensure physiologically perceived smooth and gradual motion and reversal of direction of motion. Ratios of vertical to rocking motions, range of cycles from endpoint to endpoint, acceleration/deceleration rates may vary and may be programmed, programmable, or a function of dynamic machine learning and a function of biological attributes of the user detected by sensors. A movable surface may be singular or split to accommodate more than one user and enabled with distinct motion aspects suitable to each user. A variety of actuators may be used to accomplish the motions and such actuators may include inter alia: pistons, linear actuators, rotors and gears and coupling rods or combinations thereof or any other mechanism enabled to perform the described motions. A computer or programmable control circuit may control the motions.

The actuators may be effectively in contact with a frame configured to support the surface, wherein the electronic actuator(s) may be configured to act alone or together to move the surface according to the described motion profiles. A system that operates the moveable surface may include a digital processor/controller (programmed and programmable, including remotely accessible and programmable) configured to direct the actuators in one or a plurality of predetermined or dynamic and responsive modes (as a function of biological parameters of a user and/or ambient attributes such as temperature, light and sound) of multi-directional and simultaneous motions. The system may learn which motions to effect with respect to amplitudes and cycle times/frequencies, including when and for how long, based on desired and measured user biological and/or ambient parameters. The system may include a holding mechanism, or a braking system, for holding the rocking surface or platform steady in a given position; such as a brake applied to a flywheel or piston rod.

Data collection from many users, biological parameters of the users, ambient parameters, and results of motion types and duration on user sleep attributes may be obtained through data transmission and recording means which may enable study leading to improved effectiveness of motion types or comparisons across users which may be segmented in various ways such as in accordance with sex, age, health status, lifestyle, etc.

Rocking motion may be achieved via a motor causing an axle to spin with a flywheel attached and a push-pull rod attached to the flywheel and connected to a frame wherein the rod's push-pull motion rocks the frame. Alternatively, a piston with vertical motion may push a rocking frame up or down. A cam attached to the spinning axle, and either having rollers or moving against rollers attached to a frame, may effectively rock the frame as the cam's oblong and shortened perimeters move across the rocking surface. Cams affixed to supporting and rocking surfaces and connected in a pully fashion with a belt or chain may also effect a rocking motion.

Further to the preceding description, embodiments of the present invention may include a frame configured to support a platform designed to rock head to toe on one or more pivots attached to a lower base. The device may include a stabilizing mechanism for the rocking platform when motion has ceased such as a caliper mechanism that grasps and holds a component connected to the rocking platform, a mechanism that inserts itself into the gears of a component, or of multiple components, connected to the rocking platform, and so on.

A vertical motion mechanism may comprise a lower and upper frame (e.g., base frame 20 and upper frame 70—see FIG. 1) containing a motor and actuators which may be: (i) a rotating cam of varying diameter comprised of rollers on a contact surface capable of imparting up-down movement to an upper frame as the rollers roll against a specially configured under-surface of the upper frame or a rocker arm attached to a flywheel that pushes and pulls against the upper frame; or (ii) one or more pistons capable of moving the upper frame in an up-down motion; pulleys; or (iii) a fluid bladder wherein fluid injection may impart upward movement to a frame secured above the bladder; or (iv) springs capable of compression and decompression; or other means for imparting the up-down motion. The upper frame may be secured to the lower frame by means such as sliding rails/telescoping cylinders at strategic locations or pivots or a pivot point.

The platform may be a bed, an adjustable bed base, a crib, a chair or other platform configured to receive and support a body. The motions of the upper frame are one of, or a combination of, a vertical motion and a rocking motion, wherein the pivot point(s) may be automatically moved in an up/down or lateral motion, thus enabling both the vertical and rocking motions, wherein the motion gradually accelerates from the bottom to its mid-cycle range (wherein the mid-cycle range, or approximately half amplitude in one embodiment, is variably controlled by a user or a program that may use sensor data to automatically adjust the mid-cycle range so as to achieve desired user biological parameters such as degree or duration of rapid eye movement (REM) sleep, snoring reduction, etc.) and upon reaching and exiting from said mid-cycle range gradually decelerates to a full or near stop upon reaching its programmed or determined endpoint; whereupon it gradually accelerates downward to its mid-cycle range and decelerates gradually as it approaches bottom, whereupon the upper frame may fully or nearly cease moving before resuming the upward movement.

In a variation, the up-down movement of the upper frame may comprise a period of constant period of speed (distance over time) between the periods of deceleration and acceleration of the upper frame with regard to the endpoints of the upper frame as described above.

Similarly, the head-toe rocking motion achieved as described may have the same accelerating and decelerating attributes from and to its bottom and endpoint cycles with regard to the mid-cycle range of the cycles.

The platform (e.g., upper frame) may have one or more sections, such as in a split bed, with each section capable of such movement independently or synchronized. The rocking platform itself may support or be an adjustable bed base or support for a standard mattress or crib. For example, the rocking platform may be enabled to hold varying sizes of box springs through adjustable sliding arms of the platform, on which a mattress may be placed.

The pivot points of the rocking platform may themselves be movable and moved automatically laterally along the supporting frame to change the point of the fulcrum and thus the user experience.

A combination of the vertical and rocking motions may be accomplished in varying degrees with respect to coordinating dynamics of rocking and vertical motion. The varying degrees pertain to combined ratios of cycle times, amplitudes of travel, deceleration/acceleration from end points to mid points which may be user set, pre-programmed, artificial intelligence (AI) or algorithmically determined based on user biological parameters, ambient and other data deemed relevant to desired outcomes.

Modes comprising pre-programmed cycle times, amplitudes and degrees of acceleration/deceleration, user set, or automated may be available; with the latter receiving sensor data relating to one or more user biological parameters.

The above motion and biological parameters may be driven and recorded remotely or locally by hardware/software combinations and may comprise single or multi-user databases which may be interrogated to derive desired data pertaining to use patterns, biological parameters and the like. Ambient data may be included such as noise level and type, temperature, air currents, light intensity, aromas, atmospheric pressure, seasons, times of day, circadian rhythms, etc. and disturbances that may occur caused by the user or ambient conditions and indicators of user waking versus sleep periods. Artificial intelligence (AI) may be trained to analyze the data and suggest or effect optimal motions at optimal times based on sensor readings of biological parameters of a user and/or ambient parameters.

Embodiments of the method, and associated system, computer program product and computer program include components of providing a user of the bed with a menu of motions and a database of health care sensory data collected via telemetry from the user or other users which may have similar attributes to the user, to enable a choice from the user regarding the motions over a period of time.

Reference will now be made to exemplary embodiments illustrated in the drawings and specific language will be used herein to describe the same. It will nevertheless be understood that no limitation of the scope of the disclosure is thereby intended. Alterations and further modifications of the inventive features illustrated herein and additional applications of the principles of the inventions as illustrated herein, which would occur to one skilled in the relevant art and having possession of this disclosure, are to be considered within the scope of embodiments of the present invention.

The system may include a manual or sensor-activated automatic "kill switch" in case of any unexpected incident or sensor reading that may indicate an unsafe condition and be designed to return to a level, horizontal, or pre-determined position when in the "off" position for convenience and safety.

Any of the motion aspects may be modified by programs and logic triggered by sensed changes in biological parameters of a user such as departure from a REM or desired sleep state, physical agitation or commencement of snoring. Changes to these aspects may be governed by an AI algorithm that learns which motion types tend to prolong and expedite desired biological states in a user and also to effect these motions with respect to cycle times, acceleration rates, pivot point locations, travel distances, relative combinations of vertical and rocking motions and their respective cycle time, travel and acceleration coordination.

Anticipated mechanisms of inducing motion to an upper frame may include: rotary motor, D.C gear motor, A.C. motor, drive arm, a piston, a cam, a flywheel, a slip clutch, a rocking pivot arm, a linear actuator, hydraulic, piezoelectric, electromagnetic, pulley and cable positioned at various locations including above, on a lower base and upper rocking mechanism frame to produce motion to a top base platform positioned atop the rocking mechanisms working in tandem together, and fluid chamber(s) that may be filled and emptied so as to produce motion of a proximal surface. The purpose of the motion of the upper frame is to produce desirable motions to the items to be rocked that are located atop the preceding mechanisms.

In one embodiment, a torso or leg portion of a surface may be independently driven to accomplish up-down cycles according to the motion disclosed, thus moving the upper or lower sub-surfaces independently or in a coordinated fashion. A user or a program may direct the movement, and sensors of user biological parameters may be deployed wherein movement may be a function of readings therefrom.

The user support surface must be stable in any position and support the weight of most anticipated weight distributions such as two over-weight individuals exiting from the same side or end of a bed, sitting on a side or end for example. Lateral and longitudinal support mechanisms may be implemented to secure the body support surface accordingly. This may be accomplished in the longitudinal (head/foot) rocking direction by a gear locking mechanism, braking calipers, bumper, or springs deployment for example.

An auto-level feature is desired when a user wishes to stop motion or a computer program stops the motion. A level detection mechanism may be used which, at a desired or pre-determined reading, triggers a halt in motion to secure the position of the user.

The inventive motions may be combined through a master controller, applicable programming and sensor set to effect a variety of coordinated therapies to a body on the surface through mechanized actions taken by a smart mattress itself that is equipped with embedded therapy devices.in combination with inventive motions. Systemic and programmatic integration with a smart mattress made by another manufacturer is anticipated to accomplish the foregoing.

Further aspects of the invention include positioning the head-toe pivot off-center calculated to achieve any desired degree of vertical travel for the torso or below torso portions of the body or to relieve load on the motor by achieving a more even weight distribution on a side of the pivot point. The pivot point may be adjustable manually or automatically as described herein as a function of sleep or ambient attributes. The pivot may be attached to the lower support structure or the upper rocking structure or to an external structure.

A digital camera may be programmed to observe users for a variety of attributes including movement or lack thereof, and to direct changes to the motion described herein or initiate or stop motion. Sensors described herein may be programmed to send an emergency help alert based on readings such as lack of breathing or heart rhythm or lack of beating of the heart.

A remote control and monitor may be provided for use by parents, for example of a rocking crib with programmable alerts based on sensor readings of biological attributes.

FIG. 1 depicts a side view of a rocking bed structure 100 comprising a base frame structure 15, an upper frame 70, and a mattress 80, in accordance with embodiments of the present invention. In one embodiment, the rocking bed structure 100 may be smart powered. The upper frame 70 supports the mattress 80.

In one embodiment, the mattress 80 is a smart mattress that contains one or more biological sensors 86 for measuring biological parameters of a user and/or one or more environmental sensors 87 for measuring one or more ambient parameters in a vicinity of the user.

In one embodiment, the upper frame 70 is structured as a box spring which supports the mattress 80 by being underneath the mattress 80 such that the box spring is in direct mechanical contact with the mattress 80.

The base frame structure 15 includes a base frame 20, a drive mechanism 30, a push rod 40, rocket pivoting arms 50, pivots/swivels 55 attached at various locations in the base frame 20 and used for implementing rocking motion of the upper frame 70 and the mattress 80, and pivots 65 attached at various locations in the base frame 20 and used for implementing vertical or enabling rocking motion of the upper frame 70 and the mattress 80. The base frame 20 is coupled to the upper frame 70 and is configured to impart rocking and/or vertical motion to the upper frame 70.

Thus, in one embodiment, the rocking bed structure 100 includes two separate and distinct frames, namely the base frame 20 and the upper frame 70, linked together with the upper frame 70 disposed above the base frame 20.

In one embodiment, the rocking bed structure 100 includes: one or more actuators 35 comprising (i) one or more rocking motion actuators configured to impart a rocking motion to the upper frame 70 and/or (ii) one or more vertical motion actuators configured to impart a vertical motion to the upper frame 70. One or more power sources 38 provide electrical power to the one or more actuators 35 which enables the one or more actuators 35 to impart the rocking motion and/or the vertical motion to the upper frame 70 and the mattress 80.

In one embodiment, the one or more actuators comprise devices selected from the group consisting of linear actuators, pistons, cams, flywheels, belts, springs, hydraulic devices, pulleys, gears, and combinations thereof.

The push rod 40, the rocket pivoting arms 50, the pivots 55, and the one or more rocking motion actuators are used collectively to impart a rocking motion to the upper frame 70 and the mattress 80. For example, a rocking motion actuator may be, or include, the drive mechanism 30.

The pivots 65 and the one or more vertical motion actuators 35 are used collectively to impart a vertical motion to upper frame 70 and the mattress 80. The pivots 55 and 65 collectively provide support to the upper frame 70.

In one embodiment, a kill switch 37, which is coupled to the one or more actuators 35, is configured to have the one or more actuators 35 return the upper frame 70 to a level, horizontal, or pre-determined position for convenience and/or safety, in response to a measured biological parameter of the user, and/or an environmental parameter, having a value outside of a specified range of values or a stop command from a user.

Figure 2:
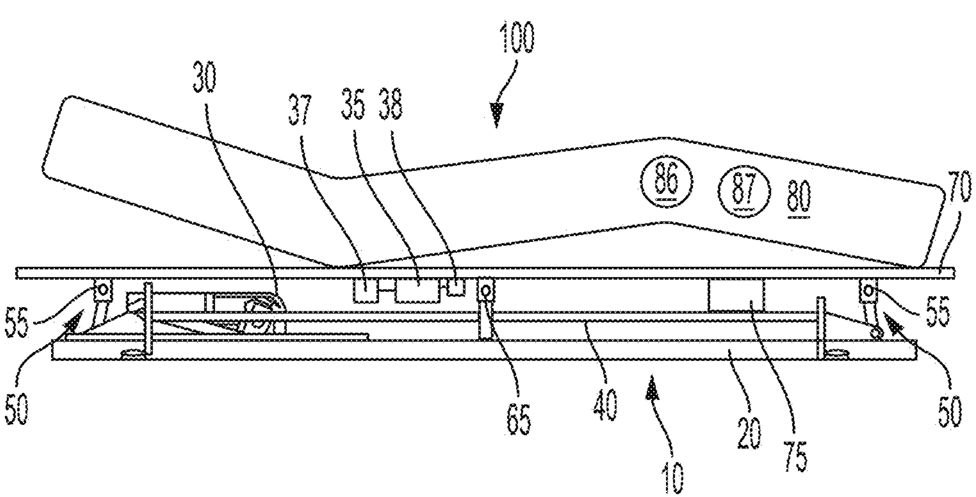
FIG. 2 depicts the side view of the rocking bed structure of FIG. 1 in which a shape of the mattress is adjustable, in accordance with embodiments of the present invention.

In one embodiment, a holding mechanism 75 depicted in FIG. 2 is configured to hold the upper frame 70 steady in a given position.

FIG. 2 depicts the side view of the rocking bed structure 100 of FIG. 1 in which a shape of the mattress 80 is adjustable, in accordance with an embodiments of the present invention. The mattress 80 is shown in FIG. 2 as resting atop the upper frame 70. If the upper frame 70 is structured as a bed frame, then a shape of the bed frame may be adjustable in one embodiment.

Figure 3:
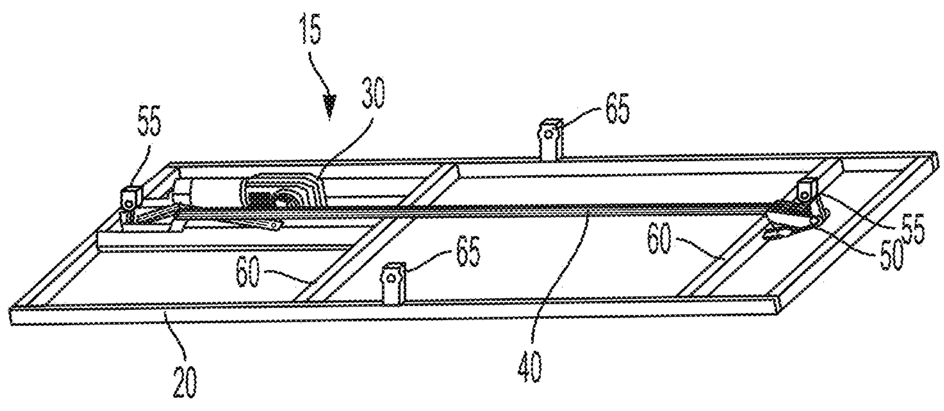
FIG. 3 is three-dimensional view of the base frame structure of the rocking bed structure of FIG. 1, in accordance with embodiments of the present invention.

FIG. 3 is three-dimensional view of the base frame structure 15 of the rocking bed structure 100 of FIG. 1, in accordance with embodiments of the present invention.

A left edge segment of the base frame 20 holds the drive mechanism 30 (which may comprise a motor; e.g., a gear motor, in one embodiment) and the rocket pivoting arm 50, which collectively effect the rocking motion of the upper frame 70. One or more structural crossbars 60 enable rigidity of the base frame 20 and support the pivots 55 which are coupled to the rocket pivoting arm 50 which connects to the upper frame 70 in a back-forth push-pull motion causing the upper frame 70 to rock.

In one embodiment, the drive mechanism 30 may comprise a motor driving a rotating cam which connects to an edge of an upper frame 70 and imparts a rocking motion to the upper frame 70 as the larger, then progressively smaller, radius portions of the drive mechanism 30 make a connection with the upper frame 70. That connection between the rotating cam and the edge of an upper frame 70 may comprise (i) a series of rollers along the outer edge of the cam which roll against a bottom of the upper frame 70 to impart a smooth motion or (ii) a belt or chain drive connecting the cam to a roller affixed to the upper frame 70. A fly wheel rotated by the motor and crank shaft may accomplish similar motion with one end of the crank shaft affixed to one edge point of the fly wheel and the other edge point of the crank shaft affixed to a swivel attached to an end of the upper frame 70.

The pivots 65, which support upper frame 70, may be powered by linear actuators, hydraulics or other means to impart controlled up-down movement to the upper frame 70. In one embodiment, a computer program may control and coordinate the up-down movement to the upper frame 70 with rocking movements of the upper frame 70.

Operation of the rocking bed structure 100 may comprise aspects that include: (i) a vertical travel distance from parallel to the floor of the ends of the rocking upper frame 70 with maximum angles achieved with respect to a reference surface parallel to a floor which supports the rocking bed structure 100; and (ii) time to complete up-down cycles or rocking speed, and (iii) the ratios or combinations of aspects (i) and (ii). The design and management of the mechanisms necessary to effect these inventive rocking and/or vertical motions of the upper frame 70 are configured to achieve a restful and/or therapeutic user experience.

The design of each of the pivot points 55 and 65, motor revolution speed, radius length and change of length of a fly wheel or cam, length and connection points of a drive arm or piston extension length may affect the degree of travel of the rocking base ends of the upper frame 70. The revolution speed, piston or linear actuator cycle rate, etc. will affect the speed or cycles per unit of time. Embodiments of the present invention span a number of possible combinations of the preceding components designed to achieve a specified or programmatically directed degree of travel and or cycle time or speed and coordination of vertical and rocking motions of the upper frame 70.

Figure 4:
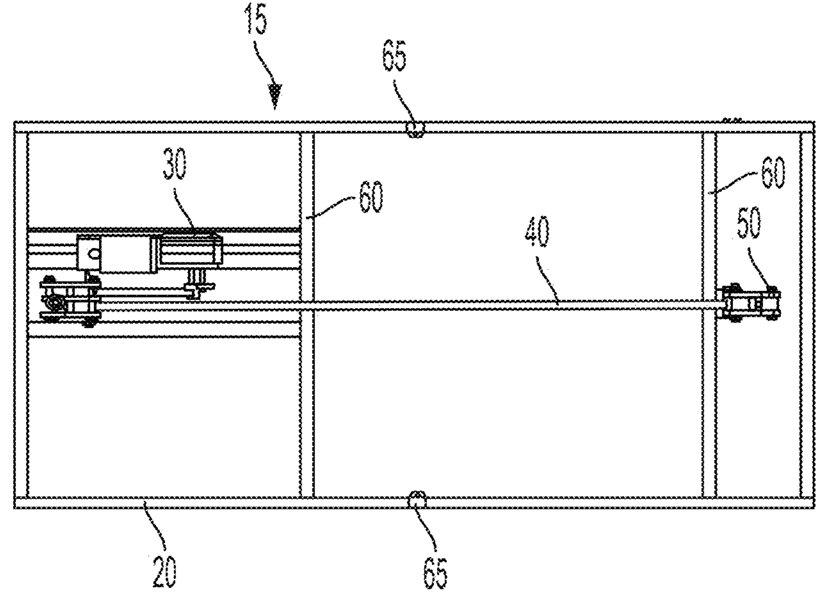
FIG. 4 is a top view of the base frame structure of FIG. 3, in accordance with embodiments of the present invention.

FIG. 4 is a top view of the base frame structure 15 of FIG. 3, in accordance with embodiments of the present invention.

Figure 5:
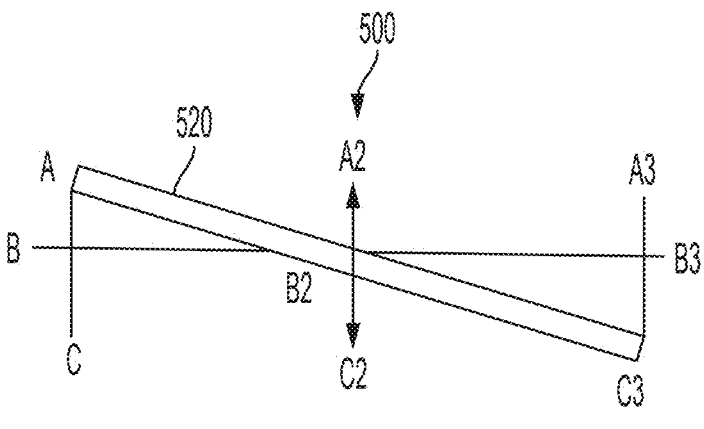
FIG. 5 depicts key elements of inventive rocking and vertical motions of a surface, in accordance with embodiments of the present invention.

FIG. 5 depicts key elements 500 of inventive rocking and vertical motions of a surface 520, in accordance with embodiments of the present invention. The surface 520 may represent, inter alia, a surface of the upper frame 70.

FIG. 5 depicts and describes key elements of the inventive rocking and vertical motions as applied to the surface 520 which rocks in a head-toe motion and may also move in a vertical motion independently or simultaneously. FIG. 5 schematically shows the type of movement in which motion of each end of the surface 520 accelerates up or down from its cycle/amplitude endpoints to their respective mid-cycle ranges, whereupon a gradual deceleration is accomplished until at the endpoint of each direction at which a full or near full stop and possible pause occurs. The same movement is accomplished for any accompanying vertical motion. Further, the ratios of degree and/or speed (distance or degrees of movement over time) for the vertical to rocking motions may vary by user choice, programming, or as a function of sensor and AI rule/learning-driven data.

More specifically in FIG. 5, the inventive rocking and vertical motions comprise the following phases: (i), (ii), (iii) and (iv) in each motion cycle and (v) for repeating the cycles: (i) imparting an increasing acceleration as change in velocity per unit of time (where velocity is measured in degrees or units of distance per unit of time) of the surface 520 from cycle endpoints A, A2, A3 toward mid-cycle ranges B, B2, B3, followed by (ii) imparting a deceleration from mid-cycle ranges B, B2, B3 to endpoints C, C2, C3 and an eventual pause or near pause of motion of the surface 520 at the endpoints C, C2, C3, followed by (iii) imparting an accelerating motion from endpoints C, C2, C3 toward mid-cycle ranges B, B2, B3, followed by (iv) imparting a decelerating motion from mid-cycle ranges B, B2, B3 toward endpoints A, A2, A3 and (v) repeating the above described transition of direction of motions (i), (ii), (iii) and (iv). The motion may be (i) either rocking or vertical motion alone or (ii) both rocking and vertical motion in combination. Range of travel to endpoints may vary as may acceleration and deceleration to and from any combination of endpoints and regions. Vertical and head-toe rocking motions may be coordinated and any desired ratio of motion types, travel ranges, ratio of cycle times, duration; etc. Although the mid-cycles ranges B, B2, B3 are represented by single points in FIG. 5, the mid-cycles ranges B, B2, B3 are generally each a continuous distribution of points. In one embodiment, however, a mid-cycle range may be arbitrarily small so as to approach a single point in size.

Although in FIG. 5, endpoints A, A2, A3 are each depicted as an apex and endpoints C, C2, C3 are each depicted as a nadir, the role of endpoints A, A2, A3 and endpoints C, C2, C3 may be interchanged in one embodiment such that endpoints A, A2, A3 are each a nadir and endpoints C, C2, C3 are each an apex. Furthermore, the inventive motion applies from any motion commencement point e.g. a head end in the lowermost, upper most or parallel to the ground positions wherein upon commencement, the described acceleration ensues until an approximate midpoint within the mid-cycle range between endpoints is reached between the motion commencement point and the apex or nadir whereupon the direction of motion changes, and a deceleration commencing at that midpoint progressing to a gradual pause or reversal of motion.

In embodiments, the one or more mechanisms used in FIG. 5 is/are a member of the group rotary or D.C gear motor, A.C. motor, a slip clutch, drive arm, a piston, a cam, a flywheel, roller bearings a rocking pivot arm, a linear actuator, hydraulic, piezoelectric, electromagnetic, pulley and cable.

In one embodiment, the rocking bed structure 100 assumes a user-selected or automatic programmed position when switched off and an automatic safety kill switch with associated trigger parameters.

An embodied method may be pre-determined and programmable. The method directs the mechanisms described herein to produce a desired one or more motion types of acceleration or deceleration, including a random acceleration or deceleration in the amplitude of a wave type motion.

At least one of a single and multiple pivot points (e.g., pivot points 55 and/or 65 in FIGS. 1-4) are located below or above the objects to be moved and include at least one stationary pivot point positioned in the approximate middle or lateral center of the rocking mechanism and the moveable one or more pivot points. Independently addressable surfaces of the disclosed bed enable each sleeper to have a different motion or none induced to their sleep surface.

The disclosed embodiments and motions as a function of inputs from biological and/or ambient data sensors may be enabled, and data obtained is stored pertaining to motion types experienced by the user and the effect on the user. The data may be associated with a user and the user's sleep and health attributes. In one embodiment, the data is used to produce desired motions upon command, automatically and/or programmatically. Motion types may be correlated to sleep states and used to optimize the user's desired sleep state such as to induce or promote continuity of such sleep state. Positions of an adjustable bed as well as motion types thereof are incorporated in the above process to combine both motion and adjustable bed positions for a user to achieve a desired state. Data is obtained from a variety of possible use and ambient condition sensors including acoustic, visual, temperature, pressure, implanted, movement, moisture, etc. Embodiments of the present invention also include automated control of settings of an adjustable bed base or smart mattress which itself may impart physical attributes to a user's body in conjunction with said one or more rocking and vertical motions aimed at impacting a desired sleep or other user biological state. For example, varying positions of an adjustable base and/or functions of a smart mattress may interact with the inventive motions of embodiments of the present invention and call for modifications of said motions in coordination with said forgoing adjustable base and smart mattress functions to better achieve or maintain desired user biological states.

A smart user device such as a phone connects with data pertaining to attributes of both bed motion and adjustment positions over periods of time. In one embodiment, the user is enabled to assign one or more scores with respect to sleep and other personal satisfaction attributes linked to the bed motion and positions and data may be used to dynamically adjust motion types and bed positions to best suit a user at any determined period of time.

In one embodiment, a database and analytic engine is configured for obtaining, storing and analyzing the data from one or more users as well as a user's health status, physiological attributes and maladies. A menu of pre-programmed motions and/or adjustable bed positions over definable time periods are associated with a user's physiological requirements or preferences. In one embodiment, pre-programming may be employed as a function of desired benefits and preferences and user physiological health profiles.

Sensors for biological parameters of a user's physiological attributes may be worn or incorporated into the rocking bed structure 100 and associated system or the mattress 80 or otherwise be in contact with the user or observe the user, and a network may communicate and/or connect with the rocking bed structure 100. The network is further capable of remote monitoring of data from the biological parameters. The network is enabled to integrate and communicate with smart devices such as computers and smart phones and other personal digital devices and networks.

In one embodiment, the user or users may be advised of ambient conditions that are conducive or adverse to optimal sleep attributes.

In one embodiment, a load balancing and support frame is operatively connected to an attachment point as a means of attaching the motion imparting mechanism to an item support frame comprising a load-bearing bar or structure configured to reduce load stress on moving joints and assemblies at points of contact.

This entire system or structure of the rocking bed structure 100 can be totally self-contained in a flatbed structure of its own or an adjustable bed structure or piece of furniture in and of itself. These systems, mechanisms or devices would be totally self-contained in one structure and covered with any number of suitable materials for aesthetic appeal and safety purposes. It is intended that this self-contained structure configuration, and more specifically the rocking bed structure 100, could also be used in a child's bed, a baby crib, an animal bed, indoor and outdoor furniture or any other number of applications. Alternatively, the structure may be provided in sections with can be connected and delivered in more than one section to reduce weight.

A mechanism is disclosed wherein one of a bumper, a damper, and a shock absorber is affixed to a motion transmission mechanism. A motion imparting mechanism may be connected to a motor and to an item frame or support point comprising: a drive arm, a cam, a piston, a spring, a flywheel, a rocking pivot arm. Embodiments of the present invention provide a unique and non-obvious method of coupling or attaching an item (e.g., a flat bed, an adjustable bed, crib, a dog bed, a piece of furniture or any other item) to an inventive rocking base that acts on any upper surface positioned atop the upper frame 70. Embodiments of the present invention use coupling methods which are ideal in light of functionality, load support and safety.

Figure 6:
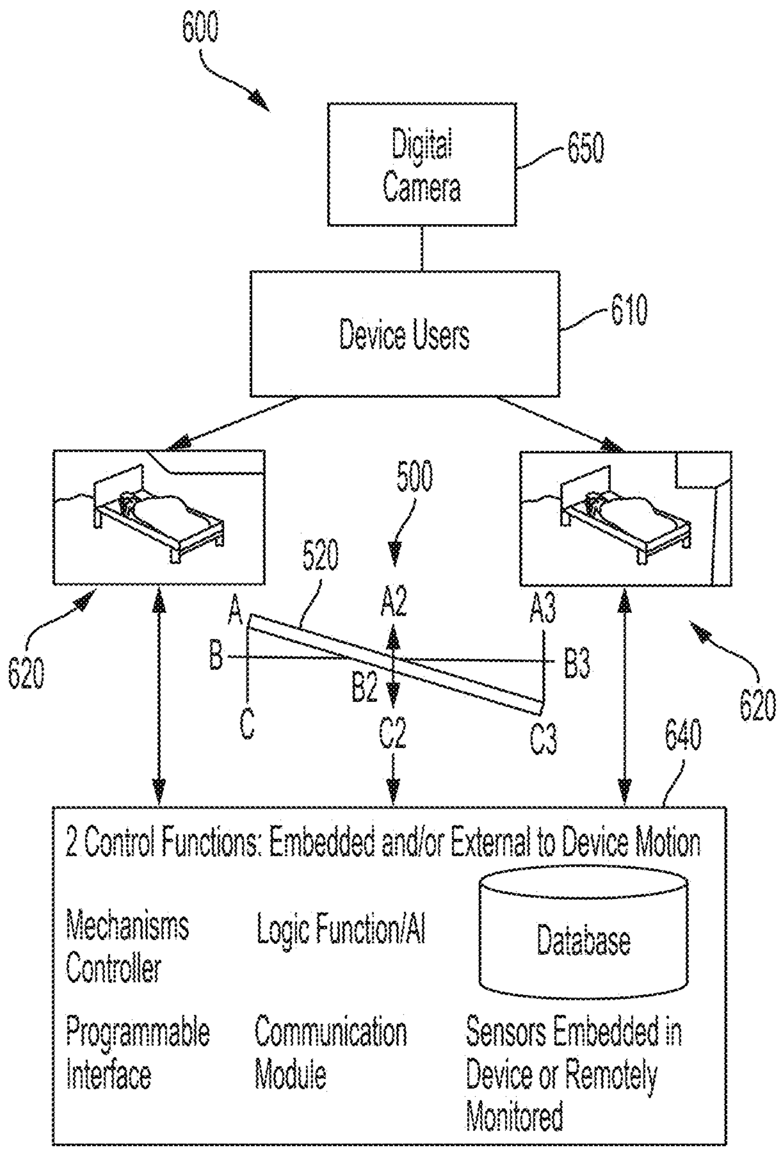
FIG. 6 depicts a system, in accordance with embodiments of the present invention.

FIG. 6 depicts a system 600, in accordance with embodiments of the present invention.

In one embodiment, the system 600 includes device users 610; motion device 620, electronic control functions 640, and a digital camera 650. FIG. 6 also depicts the key elements 500 described supra in conjunction with FIG. 5.

The motion device 620 encompasses the rocking bed structure 100 of FIGS. 1-4.

The device users 610 exhibit detectable biological parameters such as sleep state, physical movement, heart rate, electrical body activity, moisture, sounds, etc. and may be provided the ability to control aspects of the motion device 620 by interacting with the control functions 640. The motion device 620, which may be capable of the described head-toe rocking and/or vertical motions using pivot points 55 and 65, may support the mattress 80 (e.g., a smart mattress) with a variety of sensors and active functions, and may be controlled by the user such as wirelessly or by a resident or remote logic program (e.g., an AO program) that effects physical attribute changes of device function as a function of any number of parameters. The control functions 640 comprise control and communication modules which may include internal communications means to all addressable parts of the motion device 620 and external communication means such as to control and monitoring programs to which data may be sent and/or from which data and/or instructions may be received from, inter alia, a mobile device operated by a user.

Further a logic submodule may contain programs that drive the actions of the physical aspects which the motion device 620 is capable of. Such actions may be based on stored program instructions, updates, user selected programs and/or inputs from sensors of ambient characteristics and/or user biological attributes and changes in those attributes. A native or remote database may store interactions and correlations among and between user biological attributes and devices functions. A program, such as an AI program, may analyze such data to further dynamically modify device functions as a function of time, user biological attributes and changes thereof or other desired aspects.

In one embodiment, the digital camera 650 is configured to observe the user and measure at least one biological parameter of the user.

Figure 7:
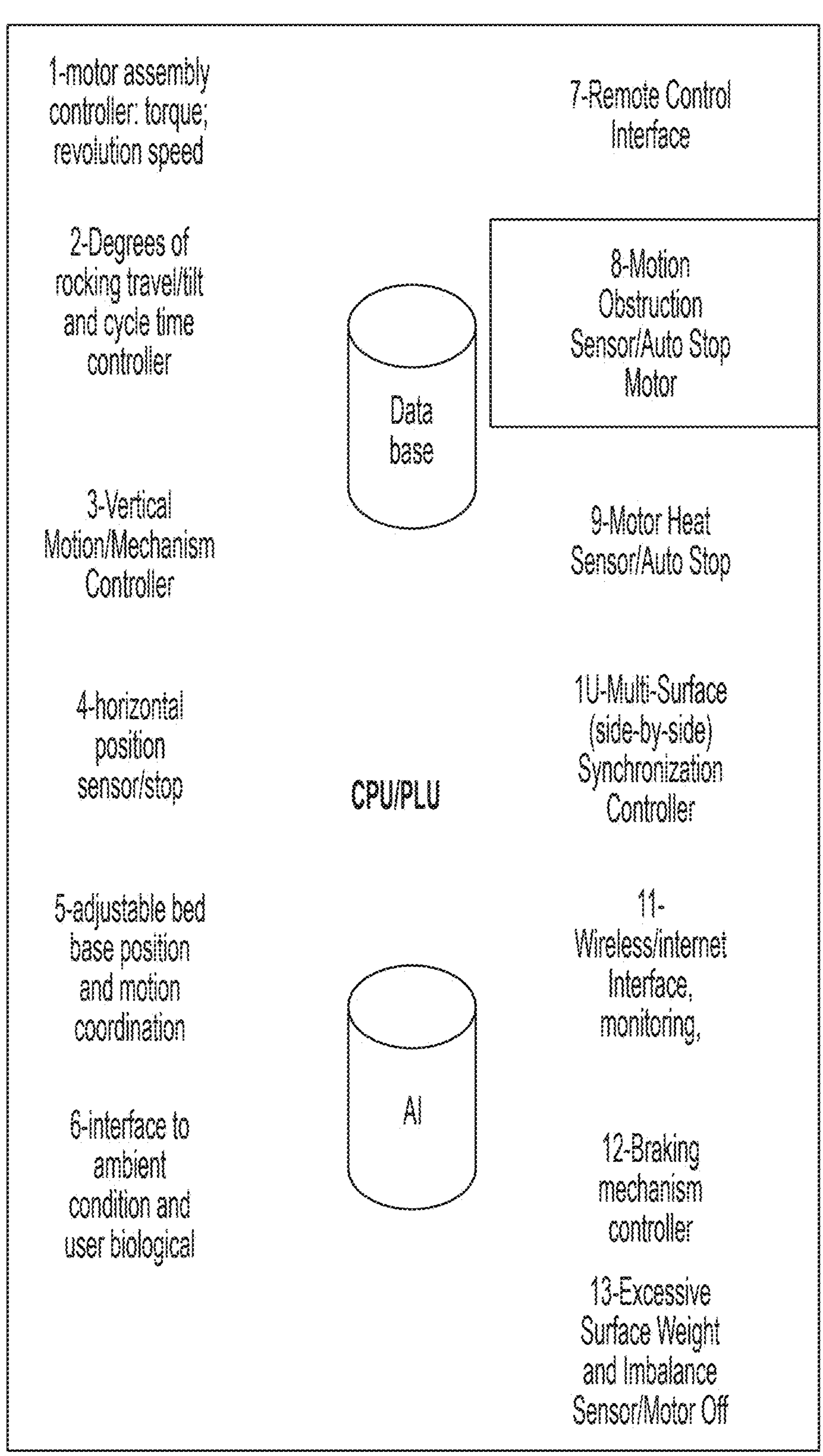
FIG. 7 includes example programs, functions, databases, controllers, and control modules, in accordance with embodiments of the present invention.

FIG. 7 includes example programs, functions, databases, controllers, and control modules, in accordance with embodiments of the present invention. An operating system of the present invention may comprise a CPU and/or PLU (Programmable Logic Unit) controlling a variety of functional aspects utilizing a motor assembly controller (1) to perform motor control that may include revolution speed/torque. Range of travel and cycle time control (2) may be achieved through motor revolution speed, changes in cam dimensions, change in piston range and speed for vertical motion, etc. A vertical motion mechanism controller (3) may include the afore-mentioned vertical motion piston or other electromechanical means of inducing cycle time and range of vertical motion changes. A horizontal position sensor and automated stop (4) in a position functions, upon being commanded or programmed, in response to, for example, specified operating time or user biological conditions. An interface to a coupled adjustable bed base (5) and its positions (and controller of same) enables automated coordination of both motion types and adjustable bed base positions if desired by a user, which may in turn be determined by association of said coordinated activity and attainment or maintenance of desired sleep states. Interface (6) to sensors of user biological conditions and ambient conditions (e.g., data such as humidity, temperature, light intensity), which data can be recorded along with sleep states and used to effect adjustable bed positions and/or device motions. Remote control interface (7) enables user control of the rocking bed structure 100. Sensors 8 and/or 9 may be used for obstructions or motor conditions under which it is advisable to automatically stop any motion, and programs that read such sensor data may direct one or more mechanisms to cease operation. Split movable surface synchronization monitor and control module (10) manages a split rocking surface for multiple users and manages on time/duration differently per side and motion types while synchronizing the surfaces when desired by users including in the all-off position so that all surfaces are parallel to the ground. An interface (11) is for external communications including mobile devices and the Internet. A control module (12) is for brake and hold mechanisms in desired positions. A sensor (13) of imbalanced weight (with respect to degree of weight and duration) across the moving surfaces may trigger programs to shut off motion to mitigate wear of motor and moving parts.

Figure 8:
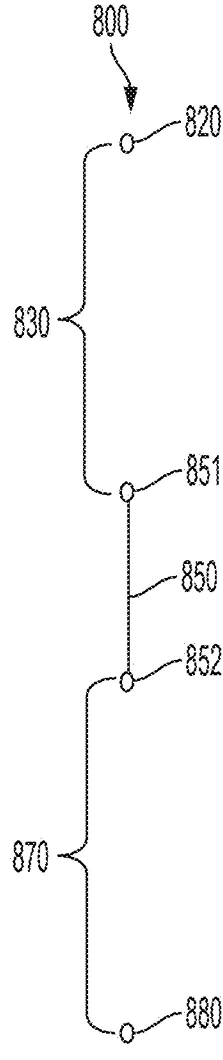
FIG. 8 depicts a range of motion of a point on the upper frame of FIG. 11 (or equivalently a point on the surface in FIG. 5), in accordance with embodiments of the present invention.

FIG. 8 depicts a range of motion 800 of a point on the upper frame 70 of FIG. 1 (or equivalently a point on the surface 520 in FIG. 5), in accordance with embodiments of the present invention.

The point on the upper frame 70 can be any point on the upper frame 70.

The range of motion 800 includes a first endpoint 820, a second endpoint 880, and a mid-cycle range of points 850 disposed between the first endpoint 820 and the second endpoint 880. The mid-cycle range 850 has a first end 851 and a second end 852. There is a first gap of points 830 between the first end 851 and the second endpoint 880. There is a second gap of points 870 between the second end 852 and the first endpoint 820.

In FIG. 8, the first endpoint 820 is represented as an apex and the second endpoint 880 is represented as a nadir. Alternatively, the first endpoint 820 could be represented as a nadir and the second endpoint 880 could be represented as an apex.

In one embodiment, the mid-cycle range 850 is equidistant from the first endpoint 820 and the second endpoint 880, which is characterized by a size of the first gap 830 being equal to a size of the second gap 870.

In one embodiment, mid-cycle range 850 is at a different distance from the first endpoint 820 than from the second endpoint 880, which is characterized by a size of the first gap 830 being unequal to a size of the second gap 870.

In one embodiment, the size of the mid-cycle range 580 (i.e., the distance between the first end 851 and the second end 852) approaches a very small value, so that the mid-cycle range 50 approaches becoming a single point, which is a midpoint between the first endpoint 820 and the second endpoint 880 if the size of the first gap 830 is equal to the size of the second gap 870.

Figure 9:
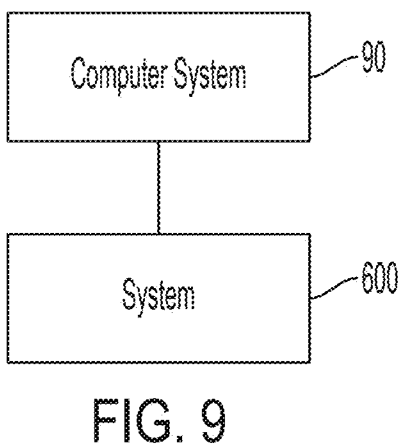
FIG. 9 depicts a computer system coupled to the system of FIG. 6, in accordance with embodiments of the present invention.

FIG. 9 depicts a computer system 90 coupled to the system 600 of FIG. 6, in accordance with embodiments of the present invention. In one embodiment, the computer system 90 is, comprises, or is comprised by, a control unit that includes the one or more processors 91 of FIG. 11 discussed infra.

The control unit is communicatively coupled to the system 600 and is thus also to the rocking bed structure 100. The control unit is configured to adjust parameters of the rocking motion and/or the vertical motion in response to measured biological parameters of a user positioned on the upper frame and/or measured ambient parameters in a vicinity of the user positioned on the upper frame.

Figure 10:
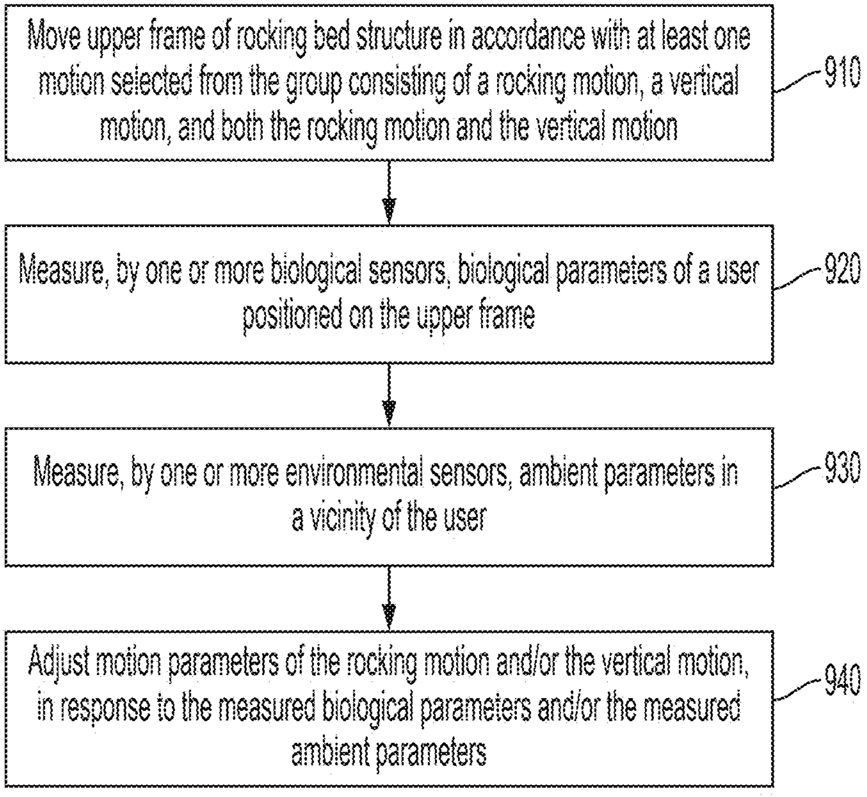
FIG. 10 is a flow chart of a method for moving an upper frame disposed within a rocking bed structure, in accordance with embodiments of the present invention.

FIG. 10 is a flow chart of a method for moving an upper frame disposed within a rocking bed structure, in accordance with embodiments of the present invention. The flow chart of FIG. 10 includes steps 910-940.

Step 910 moves the upper frame in accordance with at least one motion selected from the group consisting of a rocking motion, a vertical motion, and both the rocking motion and the vertical motion.

Each motion of the at least one motion includes each phase of the following phases (i), (ii), (iii) and (iv) occurring at least once: (i) a point on the upper frame accelerates from a first endpoint to a mid-cycle range of locations between the first endpoint and a second endpoint; (ii) the point on the upper frame decelerates from the mid-cycle range of locations to the second endpoint; (iii) the point on the upper frame accelerates from the second endpoint to the mid-cycle range of locations; and (iv) the point on the upper frame decelerates from the mid-cycle range locations to the first endpoint.

In one embodiment, each motion independently commences: at the first endpoint after which phase (i) occurs; at the second endpoint after which phase (iii) occurs; in the mid-cycle range of locations after which the point on the upper frame accelerates in the mid-cycle range of locations to an end location of the mid-cycle range of locations after which phase (ii) or phase (iv) occurs; at a first location between the first endpoint and the mid-cycle range locations after which the point on the upper frame accelerates from the first location to the mid-cycle range of locations after which phase (ii) occurs; or at a second location between the second endpoint and the mid-cycle range locations after which the point on the upper frame accelerates from the second location to the mid-cycle range of locations after which phase (iv) occurs.

In one embodiment, after completion of phase (i) or phase (iii), the upper frame moves with constant velocity in the mid-cycle range of locations to an end location of the mid-cycle range of locations after which phase (ii) or phase (iv) occurs, respectively.

In one embodiment, each motion ceases at completion of phase (i), phase (ii), phase (iii) or phase (iv) after each phase has occurred at least once.

In one embodiment, each motion that does not cease at completion of phase (ii) or phase (iv) is paused at completion of phase (ii) or phase (iv) after which phase (iii) or phase (i) occurs, respectively.

In one embodiment, each motion that does not cease at completion of phase (i) or phase (iii) is paused at completion of phase (i) or phase (iii) after which phase (ii) or phase (iv) occurs, respectively.

In one embodiment, either the first endpoint is an apex and the second endpoint is a nadir or the first endpoint is the nadir and the second endpoint is the apex.

Step 920 measures, by one or more biological sensors, biological parameters of a user positioned on the upper frame.

Step 930 measures, by one or more environmental sensors, ambient parameters in a vicinity of the user.

Step 940 adjusts motion parameters of the rocking motion and/or the vertical motion, in response to the measured biological parameters and/or the measured ambient parameters.

Next to be presented are: first embodiments pertaining to a system, second embodiments pertaining to a method for moving an upper frame disposed within a rocking bed structure, and third embodiments pertaining to computer program product.

First embodiments of the present invention pertain to a system. The system comprises: a rocking bed structure that includes an upper frame and one or more actuators configured to move the upper frame in accordance with at least one motion selected from the group consisting of a rocking motion, a vertical motion, or both the rocking motion and the vertical motion.

Each motion of the at least one motion includes each phase of the following phases (i), (ii), (iii) and (iv) occurring at least once: (i) a point on the upper frame accelerates from a first endpoint to a mid-cycle range of locations between the first endpoint and a second endpoint; (ii) the point on the upper frame decelerates from the mid-cycle range of locations to the second endpoint; (iii) the point on the upper frame accelerates from the second endpoint to the mid-cycle range of locations; and (iv) the point on the upper frame decelerates from the mid-cycle range locations to the first endpoint.

In one embodiment, wherein each motion commences: at the first endpoint after which phase (i) occurs; at the second endpoint after which phase (iii) occurs; in the mid-cycle range of locations after which the point on the upper frame accelerates in the mid-cycle range of locations to an end location of the mid-cycle range of locations after which phase (ii) or phase (iv) occurs; at a first location between the first endpoint and the mid-cycle range locations after which the point on the upper frame accelerates from the first location to the mid-cycle range of locations after which phase (ii) occurs; at a second location between the second endpoint and the mid-cycle range locations after which the point on the upper frame accelerates from the second location to the mid-cycle range of locations after which phase (iv) occurs.

In one embodiment, after completion of phase (i) or phase (iii), the upper frame moves with constant velocity in the mid-cycle range of locations to an end location of the mid-cycle range of locations after which phase (ii) or phase (iv) occurs, respectively.

In one embodiment, after completion of phase (i) or phase (iii), the upper frame moves with constant velocity in the mid-cycle range of locations to an end location of the mid-cycle range of locations after which phase (ii) or phase (iv) occurs, respectively.

In one embodiment, each motion ceases at completion of phase (i), phase (ii), phase (iii) or phase (iv) after each phase has occurred at least once.

In one embodiment, each motion that does not cease at completion of phase (ii) or phase (iv) is paused at completion of phase (ii) or phase (iv) after which phase (iii) or phase (i) occurs, respectively.

In one embodiment, each motion that does not cease at completion of phase (i) or phase (iii) is paused at completion of phase (i) or phase (iii) after which phase (ii) or phase (iv) occurs, respectively.

In one embodiment, either the first endpoint is an apex and the second endpoint is a nadir or the first endpoint is the nadir and the second endpoint is the apex.

In one embodiment, the system further comprises: one or more power sources configured to provide electrical power to the one or more actuators which enables the one or more actuators to impart the rocking motion and/or the vertical motion to the upper frame.

In one embodiment, the system further comprises: a base frame structure that comprises a base frame and one or more pivots attached to the base frame, wherein the one or more pivots collectively support the upper frame and provide pivot points for the rocking and/or vertical motion.

In one embodiment, the base frame structure further comprises a push rod and rocket pivoting arms coupled by the push rod, wherein each rocket pivoting arm couples a respective pivot of the one or more pivots to the base frame, and wherein the push rod, the rocket pivoting arms, the respective pivots, and rocking motion actuators of the one or more actuators are used collectively to impart the rocking motion to the upper frame.

In one embodiment, the base frame structure further comprises a push rod and rocket pivoting arms coupled by the push rod, wherein each rocket pivoting arm couples a respective pivot of the one or more pivots to the base frame, and wherein the push rod, the rocket pivoting arms, the respective pivots, and rocking motion actuators of the one or more actuators are used collectively to impart the rocking motion to the upper frame.

In one embodiment, the pivot points provided by the one or more pivots are movable.

In one embodiment, the system further comprises: a holding mechanism configured to hold the upper frame steady in a given position.

In one embodiment, the one or more actuators comprise one or more devices selected from the group consisting of linear actuators, pistons, cams, flywheels, belts, springs, hydraulic devices, pulleys, gears, and combinations thereof.

In one embodiment, the upper frame is a portion of: a bed, a crib, or a seat.

In one embodiment, the system further comprises: a mattress on, and supported by, the upper frame.

In one embodiment, the system further comprises: a control unit comprising one or more processors. The control unit is communicatively coupled to the rocking bed structure. The control unit is configured to adjust parameters of the rocking motion and/or the vertical motion in response to measured biological parameters of a user positioned on the upper frame and/or measured ambient parameters in a vicinity of the user positioned on the upper frame.

In one embodiment, the biological parameters are measured by one or more biological sensors and the ambient parameters are measured by one or more environmental sensors.

In one embodiment, at least one biological sensor of the one or more biological sensors is within a smart mattress resting on, and supported by, the upper frame, and wherein the at least one biological sensor is configured to measure at least one biological parameter of the biological parameters of the user positioned on the smart mattress.

In one embodiment, at least one environmental sensor of the one or more environmental sensors is external to the rocking bed structure.

In one embodiment, one biological sensor of the one or more biological sensors is configured to send an emergency help alert based on at least one biological parameter of the biological parameters of the user positioned on the upper frame being indicative of a danger to the user.

In one embodiment, the system further comprises: a digital camera configured to observe the user and measure at least one biological parameter of the biological parameters of the user.

In one embodiment, the system further comprises: a kill switch configured to return the upper frame to a level, horizontal, or pre-determined position for convenience and/or safety, in response to a measured biological parameter of the user and/or an environmental parameter having a value outside of a specified range of values.

In one embodiment, the biological parameters include parameters selected from the group consisting of sleep state, degree or duration of REM sleep, extent of snoring, blood pressure, heart rate, oxygen level, body temperature, physical movement of the user unrelated to the rocking motion and/or the vertical motion, and combinations thereof.

In one embodiment, the ambient parameters include parameters selected from the group consisting of temperature, air currents, light intensity, sound level, aromas, atmospheric pressure, humidity level, seasons, times of day, and combinations thereof.

In one embodiment, the parameters of the rocking motion and/or the vertical motion include parameters selected from the group consisting of an endpoint ratio of the vertical motion to the rocking motion, a cycle period ratio of the vertical motion to the rocking motion, vertical motion features, rates of acceleration or deceleration and combinations thereof.

The endpoint ratio of the vertical motion to the rocking motion is defined as the ratio of the spatial distance between the first and second endpoints of the vertical motion to the spatial distance between the first and second endpoints of the rocking motion.

The cycle period ratio of the vertical motion to the rocking motion is defined as the ratio of the period of each cycle of the vertical motion to the period of each cycle of the rocking motion.

The vertical motion features may include, inter alia: a head end of the upper frame (i.e., an end of the upper frame at which a user's head is located) rocks up while the apex of the vertical motion is reached; and a specified horizontal position on the upper frame is synchronized with the nadir of the vertical motion.

Second embodiments of the present invention pertain to a method for moving an upper frame disposed within a rocking bed device.

The method comprises: moving the upper frame in accordance with at least one motion selected from the group consisting of a rocking motion, a vertical motion, and both the rocking motion and the vertical motion.

Each motion of the at least one motion includes each phase of the following phases (i), (ii), (iii) and (iv) occurring at least once: (i) a point on the upper frame accelerates from a first endpoint to a mid-cycle range of locations between the first endpoint and a second endpoint; (ii) the point on the upper frame decelerates from the mid-cycle range of locations to the second endpoint; (iii) the point on the upper frame accelerates from the second endpoint to the mid-cycle range of locations; and (iv) the point on the upper frame decelerates from the mid-cycle range locations to the first endpoint.

In one embodiment, wherein each motion commences: at the first endpoint after which phase (i) occurs; at the second endpoint after which phase (iii) occurs; in the mid-cycle range of locations after which the point on the upper frame accelerates in the mid-cycle range of locations to an end location of the mid-cycle range of locations after which phase (ii) or phase (iv) occurs; at a first location between the first endpoint and the mid-cycle range locations after which the point on the upper frame accelerates from the first location to the mid-cycle range of locations after which phase (ii) occurs; at a second location between the second endpoint and the mid-cycle range locations after which the point on the upper frame accelerates from the second location to the mid-cycle range of locations after which phase (iv) occurs.

In one embodiment, after completion of phase (i) or phase (iii), the upper frame moves with constant velocity in the mid-cycle range of locations to an end location of the mid-cycle range of locations after which phase (ii) or phase (iv) occurs, respectively.

In one embodiment, after completion of phase (i) or phase (iii), the upper frame moves with constant velocity in the mid-cycle range of locations to an end location of the mid-cycle range of locations after which phase (ii) or phase (iv) occurs, respectively.

In one embodiment, each motion ceases at completion of phase (i), phase (ii), phase (iii) or phase (iv) after each phase has occurred at least once.

In one embodiment, each motion that does not cease at completion of phase (ii) or phase (iv) is paused at completion of phase (ii) or phase (iv) after which phase (iii) or phase (i) occurs, respectively.

In one embodiment, each motion that does not cease at completion of phase (i) or phase (iii) is paused at completion of phase (i) or phase (iii) after which phase (ii) or phase (iv) occurs, respectively.

In one embodiment, either the first endpoint is an apex and the second endpoint is a nadir or the first endpoint is the nadir and the second endpoint is the apex.

In one embodiment, the type of motion is the rocking motion.

In one embodiment, the type of motion is the vertical motion.

In one embodiment, the type of motion is both the rocking motion and the vertical motion.

In one embodiment, the rocking motion and the vertical motion are each a cyclic motion comprising cycles.

The cycles of the vertical motion are either in phase or out of phase with the cycles of the rocking motion.

The cycles of the vertical motion are in phase with the cycles of the rocking motion if (i) the cycles of the vertical motion and the cycles of the rocking motion have a same period (or equivalently, a same frequency) and (ii) the upper frame arrives at the first and second endpoints at the same time in the cycles of the vertical and rocking motions.

Thus, the cycles of the vertical motion are out of phase with the cycles of the rocking motion if (i) the cycles of the vertical motion and the cycles of the rocking motion have a different period (or equivalently, a different frequency) or (ii) the upper frame arrives at the first and second endpoints at different times in the cycles of the vertical and rocking motions.

In one embodiment, the cycles of the vertical motion are in phase with the cycles of the rocking motion.

In one embodiment, the cycles of the vertical motion are out of phase with the cycles of the rocking motion. In one example of this embodiment, each cycle of the vertical motion has a different period than does each cycle of the rocking motion. In another example of this embodiment, each cycle of the vertical motion has a same period as does each cycle of the rocking motion and therefore the upper frame arrives at the first and second endpoints at different times in the cycles of the vertical and rocking motions.

In one embodiment, the method further comprises: measuring, by one or more biological sensors, biological parameters of a user positioned on the upper frame; measuring, by one or more environmental sensors, ambient parameters in a vicinity of the user; and adjusting motion parameters of the rocking motion and/or the vertical motion, in response to the measured biological parameters and/or the measured ambient parameters.

In one embodiment, it is determined, employing artificial intelligence (AI) using the measured biological parameters and/or the measured ambient parameters, how to perform the adjusting of the motion parameters of the rocking motion and/or the vertical motion.

In one embodiment, the biological parameters include parameters selected from the group consisting of sleep state, degree or duration of REM sleep, extent of snoring, blood pressure, heart rate, oxygen level, body temperature, physical movement of the user unrelated to the rocking motion and/or the vertical motion, and combinations thereof.

In one embodiment, the ambient parameters include parameters selected from the group consisting of temperature, air currents, light intensity, sound level, aromas, atmospheric pressure, humidity level, seasons, times of day, and combinations thereof.

In one embodiment, the parameters of the rocking motion and/or the vertical motion include parameters selected from the group consisting of an endpoint ratio of the vertical motion to the rocking motion, a cycle period ratio of the vertical motion to the rocking motion, vertical motion features, and combinations thereof.

In one embodiment, the mid-cycle range is equidistant from the first endpoint and the second endpoint.

In one embodiment, the mid-cycle range is at a different distance from the first endpoint than from the second endpoint.

Third embodiments of the present invention pertain to a computer program product.

The computer program product comprises one or more computer readable hardware storage devices having computer readable program code stored therein. The program code contains instructions executable by one or more processors of a computer system (or of a control unit) to implement a method for moving an upper frame disposed within a rocking bed device.

The method comprises: moving the upper frame in accordance with at least one motion selected from the group consisting of a rocking motion, a vertical motion, and both the rocking motion and the vertical motion.

Each motion of the at least one motion includes each phase of the following phases (i), (ii), (iii) and (iv) occurring at least once: (i) a point on the upper frame accelerates from a first endpoint to a mid-cycle range of locations between the first endpoint and a second endpoint; (ii) the point on the upper frame decelerates from the mid-cycle range of locations to the second endpoint; (iii) the point on the upper frame accelerates from the second endpoint to the mid-cycle range of locations; and (iv) the point on the upper frame decelerates from the mid-cycle range locations to the first endpoint.

Figure 11:
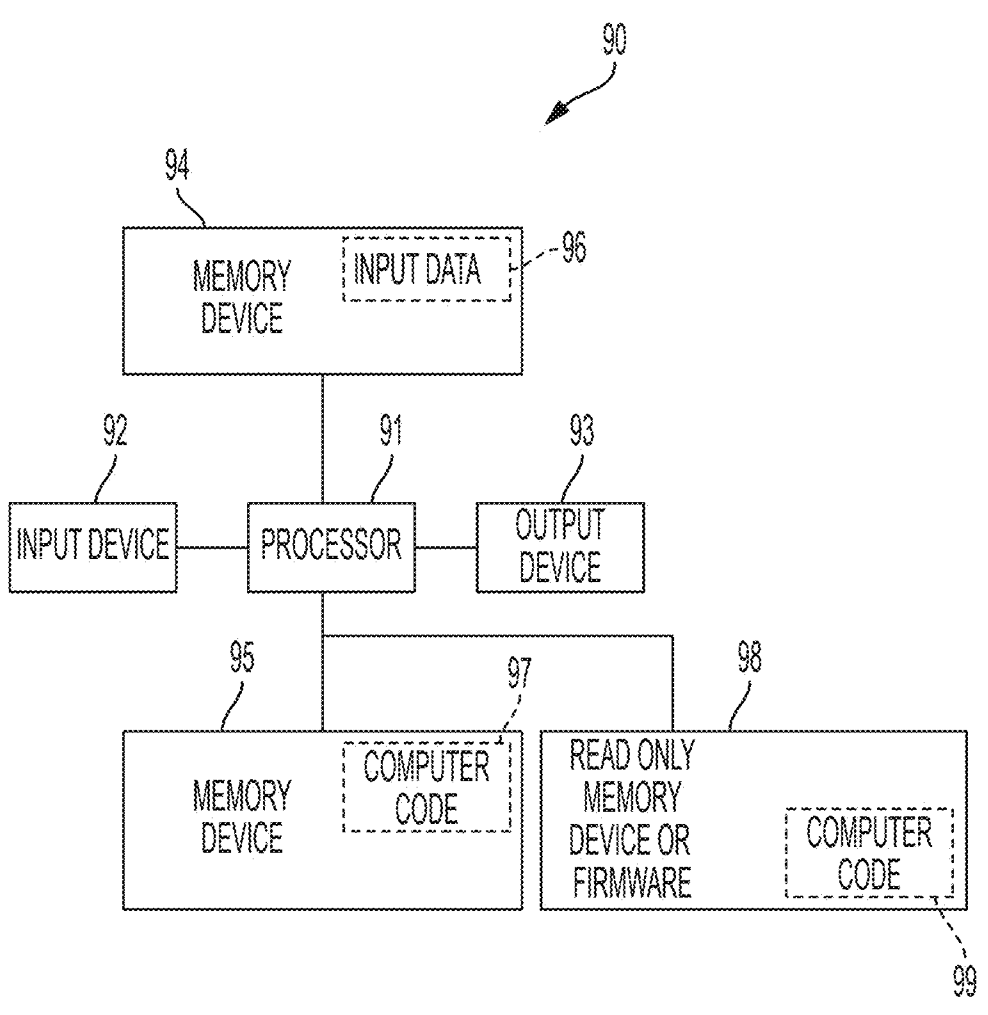
FIG. 11 illustrates a computer system, in accordance with embodiments of the present invention.

FIG. 11 illustrates the computer system 90 of FIG. 9, in accordance with embodiments of the present invention.

The computer system 90 includes a processor 91, an input device 92 coupled to the processor 91, an output device 93 coupled to the processor 91, and memory devices 94 and 95 each coupled to the processor 91. The processor 91 represents one or more processors and may denote a single processor or a plurality of processors. The input device 92 may be, inter alia, a keyboard, a mouse, a camera, a touchscreen, etc., or a combination thereof. The output device 93 may be, inter alia, a printer, a plotter, a computer screen, a magnetic tape, a removable hard disk, a floppy disk, etc., or a combination thereof. The memory devices 94 and 95 may each be, inter alia, a hard disk, a floppy disk, a magnetic tape, an optical storage such as a compact disc (CD) or a digital video disc (DVD), a dynamic random access memory (DRAM), a read-only memory (ROM), etc., or a combination thereof. The memory device 95 includes a computer code 97. The computer code 97 includes algorithms for executing embodiments of the present invention. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices such as read only memory device 96) may include algorithms and may be used as a computer usable medium (or a computer readable medium or a program storage device) having a computer readable program code embodied therein and/or having other data stored therein, wherein the computer readable program code includes the computer code 97. Generally, a computer program product (or, alternatively, an article of manufacture) of the computer system 90 may include the computer usable medium (or the program storage device).

In some embodiments, rather than being stored and accessed from a hard drive, optical disc or other writeable, rewriteable, or removable hardware memory device 95, stored computer program code 99 (e.g., including algorithms) may be stored on a static, nonremovable, read-only storage medium such as a Read-Only Memory (ROM) device 98, or may be accessed by processor 91 directly from such a static, nonremovable, read-only medium 98. Similarly, in some embodiments, stored computer program code 99 may be stored as computer-readable firmware, or may be accessed by processor 91 directly from such firmware, rather than from a more dynamic or removable hardware data-storage device 95, such as a hard drive or optical disc.

Still yet, any of the components of the present invention could be created, integrated, hosted, maintained, deployed, managed, serviced, etc. by a service supplier who offers to improve software technology associated with cross-referencing metrics associated with plug-in components, generating software code modules, and enabling operational functionality of target cloud components including modifications of the above through periodic downloads of new programming. Thus, the present invention discloses a process for deploying, creating, integrating, hosting, maintaining, and/or integrating computing infrastructure, including integrating computer-readable code into the computer system 90, wherein the code in combination with the computer system 90 is capable of performing a method for enabling a process for improving software technology associated with cross-referencing metrics associated with plug-in components, generating software code modules, and enabling operational functionality of target cloud components. In another embodiment, the invention provides a business method that performs the process steps of the invention on a subscription, advertising, and/or fee basis. That is, a service supplier, such as a Solution Integrator, could offer to enable a process for improving software technology associated with cross-referencing metrics associated with plug-in components, generating software code modules, and enabling operational functionality of target cloud components. In this case, the service supplier can create, maintain, support, etc. a computer infrastructure that performs the process steps of the invention for one or more customers. In return, the service supplier can receive payment from the customer(s) under a subscription and/or fee agreement and/or the service supplier can receive payment from the sale of advertising content to one or more third parties.

While FIG. 11 shows the computer system 90 as a particular configuration of hardware and software, any configuration of hardware and software, as would be known to a person of ordinary skill in the art, may be utilized for the purposes stated supra in conjunction with the particular computer system 90 of FIG. 11. For example, the memory devices 94 and 95 may be portions of a single memory device rather than separate memory devices.

A computer program product of the present invention comprises one or more computer readable hardware storage devices having computer readable program code stored therein, said program code containing instructions executable by one or more processors of a computer system to implement the methods of the present invention.

A computer system of the present invention comprises one or more processors, one or more memories, and one or more computer readable hardware storage devices, said one or more hardware storage devices containing program code executable by the one or more processors via the one or more memories to implement the methods of the present invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments.

What is claimed is:

1. A system, said system comprising:

a rocking bed structure that includes an upper frame and one or more actuators configured to move the upper frame in accordance with at least one motion selected from the group consisting of a rocking motion, a vertical motion, and both the rocking motion and the vertical motion, wherein each motion of the at least one motion includes each phase of the following phases (i), (ii), (iii) and (iv) occurring at least once:

(i) a point on the upper frame accelerates from a first endpoint to a mid-cycle range of locations between the first endpoint and a second endpoint;

(ii) the point on the upper frame decelerates from the mid-cycle range of locations to the second endpoint;

(iii) the point on the upper frame accelerates from the second endpoint to the mid-cycle range of locations; and (iv) the point on the upper frame decelerates from the mid-cycle range locations to the first endpoint, wherein the rocking bed structure includes a level detection mechanism configured to return the upper frame to a level, horizontal position, wherein the rocking bed structure includes a pivot attached to the upper frame in an off-center position and one or more vertical motion actuators of the one or more actuators configured to achieve, during the rocking motion, designed ratios of vertical travel distance and vertical travel cycle time at a head end and a foot end of the upper frame and of associated maximum angles of the upper frame with respect to a reference surface parallel to a floor, and wherein a commencement of motion of the upper frame from parallel to a ground or floor at a commencement point is characterized by acceleration of the upper frame from the commencement point to a mid-point of the mid-cycle range to the first end point, followed by deceleration of the upper frame from the mid-point to the first endpoint, followed by commencement of phases (i)-(iv).

2. The system of claim 1, wherein after completion of phase (i) or phase (iii), the upper frame moves with constant velocity in the mid-cycle range of locations to an end location of the mid-cycle range of locations after which phase (ii) or phase (iv) occurs, respectively.

3. The system of claim 1, wherein each motion ceases at completion of phase (i), phase (ii), phase (iii) or phase (iv) after each phase has occurred at least once.

4. The system of claim 3, wherein each motion that does not cease at completion of phase (ii) or phase (iv) is paused at completion of phase (ii) or phase (iv) after which phase (iii) or phase (i) occurs, respectively.

5. The system of claim 3, wherein each motion that does not cease at completion of phase (i) or phase (iii) is paused at completion of phase (i) or phase (iii) after which phase (ii) or phase (iv) occurs, respectively.

6. The system of claim 1, said system further comprising:

one or more power sources configured to provide electrical power to the one or more actuators which enables the one or more actuators to impart the rocking motion and/or the vertical motion to the upper frame and a base frame structure that comprises a base frame and one or more pivots attached to the base frame, wherein the one or more pivots collectively support the upper frame and provide pivot points for the rocking and/or vertical motion.

7. The system of claim 6, wherein the base frame structure further comprises a push rod and rocket pivoting arms coupled by the push rod, wherein each rocket pivoting arm couples a respective pivot of the one or more pivots to the base frame, and wherein the push rod, the rocket pivoting arms, the respective pivots, and rocking motion actuators of the one or more actuators are used collectively to impart the rocking motion to the upper frame.

8. The system of claim 1, wherein the upper frame is a portion of: a bed, a crib, or a seat.

9. The system of claim 1, said system further comprising:

a control unit comprising one or more processors, said control unit being communicatively coupled to the rocking bed structure, said control unit configured to adjust parameters of the rocking motion and/or the vertical motion in response to measured biological parameters of a user positioned on the upper frame and/or measured ambient parameters in a vicinity of the user positioned on the upper frame.

10. The system of claim 9, wherein the biological parameters are measured by one or more biological sensors and the ambient parameters are measured by one or more environmental sensors.

11. The system of claim 10, wherein at least one biological sensor of the one or more biological sensors is within a smart mattress resting on, and supported by, the upper frame, and wherein the at least one biological sensor is configured to measure at least one biological parameter of the biological parameters of the user positioned on the smart mattress.

12. The system of claim 10, wherein one biological sensor of the one or more biological sensors is configured to send an emergency help alert based on at least one biological parameter of the biological parameters of the user positioned on the upper frame being indicative of a danger to the user.

13. The system of claim 9, wherein the level detection mechanism comprises a kill switch configured to return the upper frame to the level, horizontal position, or to a predetermined position, for convenience and/or safety, in response to a measured biological parameter of the user and/or an environmental parameter having a value outside of a specified range of values.

14. A method for moving an upper frame disposed within a rocking bed structure, said method comprising:

moving, by one or more actuators, the upper frame in accordance with at least one motion selected from the group consisting of a rocking motion, a vertical motion, and both the rocking motion and the vertical motion, wherein each motion of the at least one motion includes each phase of the following phases (i), (ii), (iii) and (iv) occurring at least once:

(i) a point on the upper frame accelerates from a first endpoint to a mid-cycle range of locations between the first endpoint and a second endpoint;

(ii) the point on the upper frame decelerates from the mid-cycle range of locations to the second endpoint;

(iii) the point on the upper frame accelerates from the second endpoint to the mid-cycle range of locations; and (iv) the point on the upper frame decelerates from the mid-cycle range locations to the first endpoint; and commencing motion of the upper frame from parallel to a ground or floor at a commencement point is characterized by acceleration of the upper frame from the commencement point to a mid-point of the mid-cycle range to the first end point, followed by deceleration of the upper frame from the mid-point to the first endpoint, followed by commencement of phases (i)-(iv), wherein the rocking bed structure includes a level detection mechanism configured to return the upper frame to a level, horizontal position; and wherein the rocking bed structure includes a pivot attached to the upper frame in an off-center position and one or more vertical motion actuators of the one or more actuators configured to achieve, during the rocking motion, designed ratios of vertical travel distance and vertical travel cycle time at a head end and a foot end of the upper frame and of associated maximum angles of the upper frame with respect to a reference surface parallel to a floor.

15. The method of claim 14, wherein after completion of phase (i) or phase (iii), the upper frame moves with constant velocity in the mid-cycle range of locations to an end location of the mid-cycle range of locations after which phase (ii) or phase (iv) occurs, respectively.

16. The method of claim 14, wherein each motion ceases at completion of phase (i), phase (ii), phase (iii) or phase (iv) after each phase has occurred at least once.

17. The method of claim 16, wherein each motion that does not cease at completion of phase (ii) or phase (iv) is paused at completion of phase (ii) or phase (iv) after which phase (iii) or phase (i) occurs, respectively.

18. The method of claim 17, wherein each motion that does not cease at completion of phase (i) or phase (iii) is paused at completion of phase (i) or phase (iii) after which phase (ii) or phase (iv) occurs, respectively.

19. The method of claim 14, wherein the at least one motion is the rocking motion.

20. The method of claim 14, wherein the at least one motion is the vertical motion.

21. The method of claim 14, wherein the at least one motion is both the rocking motion and the vertical motion, and wherein the rocking motion and the vertical motion are each a cyclic motion comprising cycles.

22. The method of claim 21, wherein the cycles of the vertical motion are in phase with the cycles of the rocking motion.

23. The method of claim 21, wherein the cycles of the vertical motion are out of phase with the cycles of the rocking motion.

24. The method of claim 14, said method further comprising:

measuring, by one or more biological sensors, biological parameters of a user positioned on the upper frame;

measuring, by one or more environmental sensors, ambient parameters in a vicinity of the user; and adjusting motion parameters of the rocking motion and/or the vertical motion, in response to the measured biological parameters and/or the measured ambient parameters.

25. The method of claim 24, wherein the biological parameters include parameters selected from the group consisting of sleep state, degree or duration of REM sleep, extent of snoring, blood pressure, heart rate, oxygen level, body temperature, physical movement of the user unrelated to the rocking motion and/or the vertical motion, and combinations thereof.

26. The method of claim 24, wherein the ambient parameters include parameters selected from the group consisting of temperature, air currents, light intensity, sound level, aromas, atmospheric pressure, humidity level, seasons, times of day, and combinations thereof.

27. The method of claim 24, wherein the parameters of the rocking motion and/or the vertical motion include parameters selected from the group consisting of an endpoint ratio of the vertical motion to the rocking motion, a cycle time ratio of the vertical motion to the rocking motion, vertical motion features, and combinations thereof.

28. A computer program product, comprising one or more computer readable hardware storage devices having computer readable program code stored therein, said program code containing instructions executable by one or more processors of a computer system to implement a method for moving an upper frame disposed within a rocking bed structure, said method comprising:

moving, by one or more actuators, the upper frame in accordance with at least one motion selected from the group consisting of a rocking motion, a vertical motion, and both the rocking motion and the vertical motion, wherein each motion of the at least one motion includes each phase of the following phases (i), (ii), (iii) and (iv) occurring at least once:

(i) a point on the upper frame accelerates from a first endpoint to a mid-cycle range of locations between the first endpoint and a second endpoint;

(ii) the point on the upper frame decelerates from the mid-cycle range of locations to the second endpoint;

(iii) the point on the upper frame accelerates from the second endpoint to the mid-cycle range of locations; and (iv) the point on the upper frame decelerates from the mid-cycle range locations to the first endpoint; and commencing motion of the upper frame from parallel to a ground or floor at a commencement point is characterized by acceleration of the upper frame from the commencement point to a mid-point of the mid-cycle range to the first end point, followed by deceleration of the upper frame from the mid-point to the first endpoint, followed by commencement of phases (i)-(iv), wherein the rocking bed structure includes a level detection mechanism configured to return the upper frame to a level, horizontal position; and wherein the rocking bed structure includes a pivot attached to the upper frame in an off-center position and one or more vertical motion actuators of the one or more actuators configured to achieve, during the rocking motion, designed ratios of vertical travel distance and vertical travel cycle time at a head end and a foot end of the upper frame and of associated maximum angles of the upper frame with respect to a reference surface parallel to a floor.

* * * * *